(12) United States Patent
Boutjdir et al.

(10) Patent No.: US 11,787,840 B2
(45) Date of Patent: Oct. 17, 2023

(54) COMPOSITIONS AND METHODS FOR TREATING AND PREVENTING AUTOIMMUNE INDUCED CARDIAC LONG QT SYNDROME

(71) Applicants: The United States Government As Represented By The Department of Veterans Affairs, Washington, DC (US); NEW YORK UNIVERSITY, New York, NY (US)

(72) Inventors: Mohamed Boutjdir, Brooklyn, NY (US); Timothy Jude Cardozo, New York, NY (US)

(73) Assignees: THE UNITED STATES GOVERNMENT AS REPRESENTED BY THE DEPARTMENT OF VETERANS AFFAIRS, Washington, DC (US); NEW YORK UNIVERSITY, New York, NY (US)

(*) Notice: Subject to any disclaimer, the term of this patent is extended or adjusted under 35 U.S.C. 154(b) by 0 days.

(21) Appl. No.: 17/637,614

(22) PCT Filed: Aug. 21, 2020

(86) PCT No.: PCT/US2020/047317
§ 371 (c)(1),
(2) Date: Feb. 23, 2022

(87) PCT Pub. No.: WO2021/041177
PCT Pub. Date: Mar. 4, 2021

(65) Prior Publication Data
US 2022/0267381 A1    Aug. 25, 2022

Related U.S. Application Data

(60) Provisional application No. 62/890,947, filed on Aug. 23, 2019.

(51) Int. Cl.
*C07K 14/00* (2006.01)
*C07K 16/18* (2006.01)
*A61K 39/00* (2006.01)

(52) U.S. Cl.
CPC .............. *C07K 14/00* (2013.01); *C07K 16/18* (2013.01); *A61K 39/00* (2013.01)

(58) Field of Classification Search
None
See application file for complete search history.

(56) References Cited

U.S. PATENT DOCUMENTS

2006/0084102 A1 * 4/2006 Dougherty ........... C07K 14/705
                                                         435/325
2009/0047703 A1    2/2009 Trudeau

FOREIGN PATENT DOCUMENTS

WO    WO1998-056915    12/1998
WO    WO 2017/015119 A1    1/2017

OTHER PUBLICATIONS

U.S. Appl. No. 62/890,947, filed Aug. 23, 2019, Mohamed Boutjdir.
PCT, PCT/US2020/047317 (WO 2021/041177), Aug. 21, 2020 (Mar. 4, 2021), Mohamed Boutjdir (United States Government as Represented by the Department of Veterans Affairs).
Fabris, et al. Induction of autoimmune response to extracellular loop of the HERG channel pore induces QTc prolongation in guinea-pigs. J. Physiol., vol. 594, No. 21, pp. 6175-6187, Jun. 14, 2016.
International Search Report and Written Opinion dated Feb. 3, 2021 by the International Searching Authority for International Application No. PCT/US2020/047317, filed on Aug. 21, 2020 and published as WO 2021/041177 dated Mar. 4, 2021 (Applicant—United States Government as Represented By the Department of Veterans Affairs) (14 Pages).
Defendenti et al. Clinical and laboratory aspects of Ro/SSA-52 autoantibodies, Autoimmunity Reviews, 10 (2011), pp. 150-154.
Torres, et al. Structure of the HERG K+ Channel S5P Extracellular Linker, Journal of Biological Chemistry, vol. 278, No. 43, Oct. 24, 2003, pp. 42136-42148.

* cited by examiner

*Primary Examiner* — Adam Weidner
(74) *Attorney, Agent, or Firm* — Ballard Spahr LLP

(57) ABSTRACT

Disclosed herein, are decoy peptides or polypeptides capable of neutralizing and/or inhibiting the binding of anti-Ro antibodies to a hERG potassium channel extracellular pore region, and pharmaceutical compositions containing the decoy peptides or polypeptides and methods of use.

5 Claims, 5 Drawing Sheets
Specification includes a Sequence Listing.

COMPOSITIONS AND METHODS FOR TREATING AND PREVENTING AUTOIMMUNE INDUCED CARDIAC LONG QT SYNDROME

CROSS REFERENCE TO RELATED APPLICATIONS

This application claims the benefit of priority under 35 U.S.C. § 371 of International Application No. PCT/US2020/047317, filed Aug. 21, 2020, which claims the benefit of the filing date of U.S. Provisional Application No. 62/890,947, filed Aug. 23, 2019. The content of these earlier filed applications is hereby incorporated by reference in its entirety.

INCORPORATION OF THE SEQUENCE LISTING

The present application contains a sequence listing that is submitted via EFS-Web concurrent the filing of this application, containing the file name "37759_0233U2_Sequence_Listing.txt," which is 4,096 bytes in size created on Jan. 4, 2022, and is hereby incorporated by reference in its entirety pursuant to 37 C.F.R. § 1.52(e)(5).

BACKGROUND

Autoimmune diseases (AD) and related cardiovascular (CV) adverse outcomes are prevalent in U.S. veterans and worldwide and are increasingly recognized as a major health problem associated with significant morbidity and mortality. The National Institutes of Health (NIH) estimates up to 23.5 million Americans suffer from AD and up to 24 million from heart diseases. As a result, NIH and the American Heart Association estimate the annual direct health care costs for AD to be in the range of $100 billion and $200 billion for heart and stroke diseases. Thus, alternative therapies directed at reducing, treating or preventing complications in subjects with or at risk for AD and related cardiovascular outcomes is urgently needed.

SUMMARY

Described herein are decoy peptides comprising or consisting of the sequence of GNMEQPHMDSRIGWLHNLGDQIGKPYNSSGL (SEQ ID NO: 9), or a fragment thereof.

Disclosed herein are methods of treating corrected QT (QTc) prolongation, the methods comprising: administering to a subject with QTc prolongation a therapeutically effective amount of a decoy peptide comprising or consisting of the amino acid sequence of GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), GDQIGKPYNSSGL (SEQ ID NO: 8), GNMEQPHMDSRIGWLHNLG DQIGKPYNSSGL (SEQ ID NO: 9), or a fragment of SEQ ID NO: 9.

Disclosed herein are methods of preventing corrected QT (QTc) prolongation, the methods comprising: administering to a subject a therapeutically effective amount of a decoy peptide comprising or consisting of the amino acid sequence of GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), GDQIGKPYNSSGL (SEQ ID NO: 8), or GNMEQPHMDSRIGWLHNLGDQIGKPYNSSGL (SEQ ID NO: 9) or a fragment thereof.

Disclosed herein are methods of ameliorating one or more symptoms of corrected QT (QTc) prolongation, the methods comprising: administering to a subject a therapeutically effective amount of a decoy peptide comprising or consisting of the amino acid sequence of GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), GDQIGKPYNSSGL (SEQ ID NO: 8), or GNMEQPHMDSRIGWLHNLGDQIGKPYNSSGL (SEQ ID NO: 9) or a fragment thereof.

Disclosed herein are methods of reducing the risk of ventricular tachycardia, the methods comprising: administering to a subject a therapeutically effective amount of a decoy peptide comprising or consisting of the amino acid sequence of GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), GDQIGKPYNSSGL (SEQ ID NO: 8), or GNMEQPHMDSRIGWLHNLGDQIGKPYNSSGL (SEQ ID NO: 9) or a fragment thereof.

Disclosed herein are methods of competitively inhibiting the binding of anti-Ro antibodies to the human Ether-à-go-go-Related Gene potassium (hERG-K) channel extracellular pore region, the methods comprising: administering to a subject a therapeutically effective amount of a decoy peptide comprising or consisting of the amino acid sequence of GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), GDQIGKPYNSSGL (SEQ ID NO: 8), GNMEQPHMDSRIGWLHNLG DQIGKPYNSSGL (SEQ ID NO: 9), or a fragment of SEQ ID NO: 9.

Disclosed herein are compositions comprising a fibronectin type III (Fn3) monobody and a decoy peptide comprising or consisting of GNMEQPHMDSRIGWLHNLGDQIGKPYNSSGL (SEQ ID NO: 9), or a fragment thereof.

BRIEF DESCRIPTION OF THE DRAWINGS

FIG. 3A shows the structure of isolated peptide 4 by ab initio folding. FIG. 3B shows the structure of fusion of peptide 4 to monobody N-terminus. FIG. 3C shows the structure of fusion of peptide 4 to monobody C-terminus.

DETAILED DESCRIPTION

Figure 1:
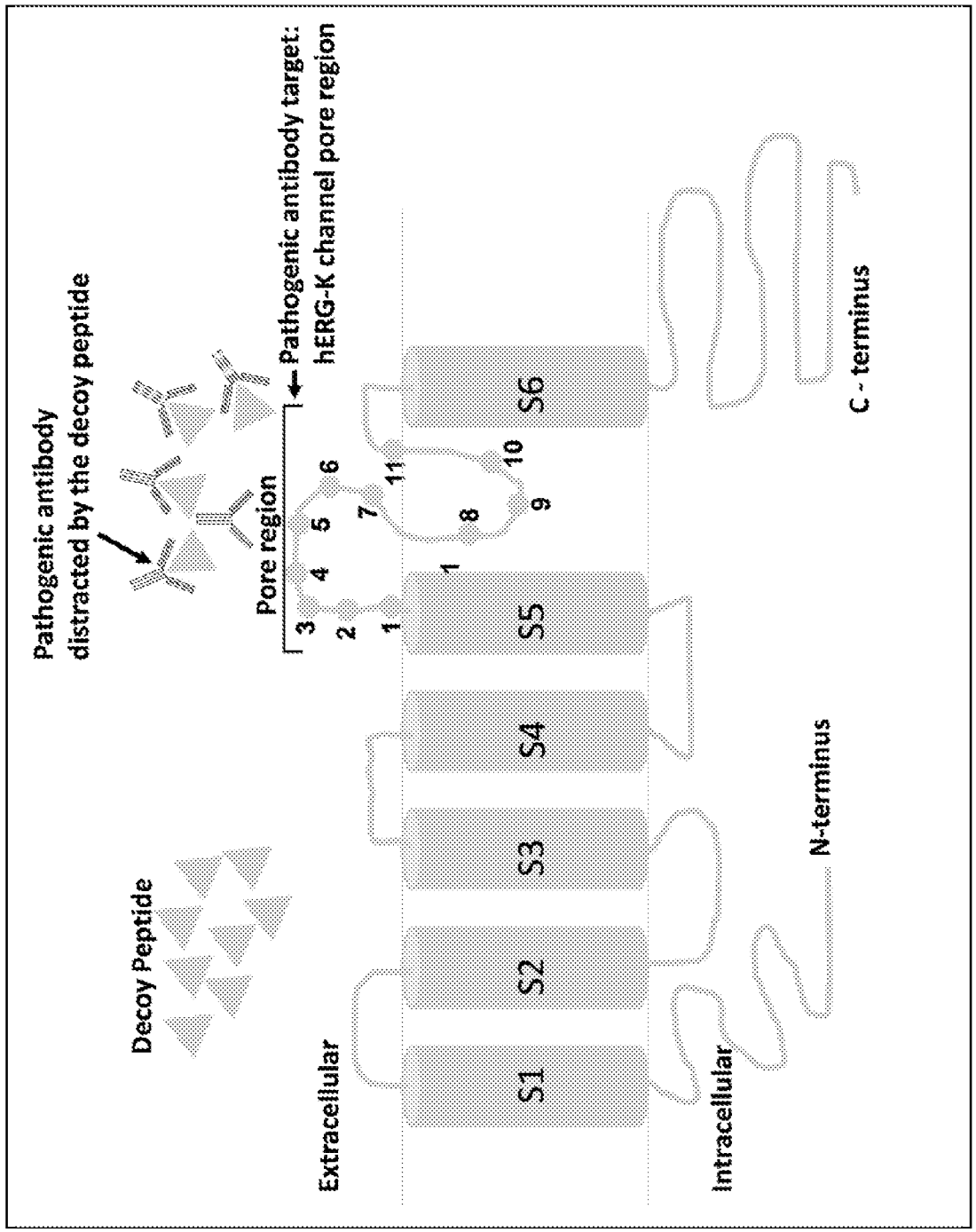
FIG. 1 is a schematic illustrating how decoy peptides can distract pathogenic antibodies from targeting the hERG-K channel. Also shown is a schematic representation of the secondary structure of a single hERG-K channel α1 subunit. The 6 segments (S1-S6) are shown, along with the intracellularly located N and C termini. The pore-forming extracellular loop is located between S5 and S6, where circles 1-4, 6, and 9 and circles 5, 7-8, and 10-11 indicate similar and corresponding amino acids (aa) between the 52-kDa Ro (52Ro) protein and hERG-K channel, respectively.

The present disclosure can be understood more readily by reference to the following detailed description of the invention, the figures and the examples included herein.

Before the present methods and compositions are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g., a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus, the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease, disorder or condition or at risk for a disease, disorder or condition. The term "patient" includes human and veterinary subjects. In some aspects of the disclosed methods, the "patient" has been diagnosed with a need for treatment, such as, for example, prior to the administering step.

As used herein, the term "comprising" can include the aspects "consisting of" and "consisting essentially of."

As used herein the terms "amino acid" and "amino acid identity" refers to one of the 20 naturally occurring amino acids or any non-natural analogues that may be in any of the variants, peptides or fragments thereof disclosed. Thus "amino acid" as used herein means both naturally occurring and synthetic amino acids. For example, homophenylalanine, citrulline and norleucine are considered amino acids for the purposes of the invention. "Amino acid" also includes amino acid residues such as proline and hydroxyproline. The side chain may be in either the (R) or the (S) configuration. If non-naturally occurring side chains are used, non-amino acid substituents may be used, for example to prevent or retard in vivo degradation.

"Inhibit," "inhibiting" and "inhibition" mean to diminish or decrease an activity, level, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100%, or any amount of reduction in between as compared to native or control levels. In an aspect, the inhibition or reduction is 10-20, 20-30, 30-40, 40-50, 50-60, 60-70, 70-80, 80-90, or 90-100% as compared to native or control levels. In an aspect, the inhibition or reduction is 0-25, 25-50, 50-75, or 75-100% as compared to native or control levels.

"Treatment" and "treating" refer to administration or application of a therapeutic agent (e.g., a decoy peptide or polypeptide described herein) to a subject or performance of a procedure or modality on a subject for the purpose of obtaining a therapeutic benefit of a disease or health-related condition. For example, a treatment may include administration of a pharmaceutically effective amount of a decoy peptide or polypeptide that inhibits the binding of anti-Ro antibodies to a human Ether-à-go-go-Related Gene (hERG) potassium channel extracellular pore region.

As used herein, the term "treating" refers to partially or completely alleviating, ameliorating, relieving, delaying onset of, inhibiting or slowing progression of, reducing severity of, and/or reducing incidence of one or more symptoms or features of a particular disease, disorder, and/or condition. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. For example, the disease, disorder, and/or condition can be QTc prolongation or ventricular tachycardia. In some aspects, the subject has an autoimmune disease, hypokalemia or hypomagnesemia.

The term "fragment" can refer to a portion (e.g., at least 4, 5, 6, 7, 8, 9, 10, 11, 12, 13, 14, 15, 16, 17, 18, 19, 20, 21, 22, 23, 24, 25, 26, 27, 28, 29, 30, etc. amino acids) of a peptide that is substantially identical to a reference peptide and retains the biological activity of the reference. In some aspects, the fragment or portion retains at least 50%, 75%, 80%, 85%, 90%, 95% or 99% of the biological activity of the reference peptide described herein. Further, a fragment of a referenced peptide can be a continuous or contiguous portion of the referenced polypeptide (e.g., a fragment of a peptide that is ten amino acids long can be any 2-9 contiguous residues within that peptide).

A "variant" can mean a difference in some way from the reference sequence other than just a simple deletion of an N- and/or C-terminal amino acid residue or residues. Where the variant includes a substitution of an amino acid residue, the substitution can be considered conservative or non-conservative. Conservative substitutions are those within the following groups: Ser, Thr, and Cys; Leu, Ile, and Val; Glu and Asp; Lys and Arg; Phe, Tyr, and Trp; and Gln, Asn, Glu, Asp, and His. Variants can include at least one substitution and/or at least one addition, there may also be at least one deletion. Variants can also include one or more non-naturally occurring residues. For example, variants may include selenocysteine (e.g., seleno-L-cysteine) at any position, including in the place of cysteine. Many other "unnatural" amino acid substitutes are known in the art and are available from commercial sources. Examples of non-naturally occurring amino acids include D-amino acids, amino acid residues having an acetylaminomethyl group attached to a sulfur atom of a cysteine, a pegylated amino acid, and omega amino acids of the formula $NH_2(CH_2)_nCOOH$ wherein n is 2-6 neutral, nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties of proline.

As used herein, the term "prevent" or "preventing" refers to preventing in whole or in part, or ameliorating or controlling.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

INTRODUCTION

QTc prolongation on the surface electrocardiogram (ECG) predisposes patients to lethal polymorphic ventricular arrhythmias called Torsades de Pointes which can lead to sudden cardiac death (El-Sherif N, et al., Pacing Clin Electrophysiol. 2018 April; 41(4):414-421; El-Sherif N and Boutjdir M; Pharmacol Ther. 2015; 155:132-42; Lazzerini P E, et al., Nat Rev Immunol. 2019 January; 19(1):63-64.2; Lazzerini P E, et al., Nat Rev Cardiol. 2017 September; 14 (9):521-535; and Capecchi P L, et al., Heart Rhythm. 2019 Feb. 14). An autoimmune acquired QTc prolongation has been reported in patients carrying anti-Ro antibodies (Abs) (Lazzerini P E, et al., Arthritis Rheum. 2004; 50:1248-52; Lazzerini P E, et al., Front Cardiovasc Med. 2016; 3:31; and Bourre-Tessier J, et al., Arthritis Care Res (Hoboken). 2011; 63:1031-7) and its functional and molecular pathogenesis was recently characterized (Yue Y, et al., Circulation. 2015; 132:230-40). Anti-Ro Abs are the results of an autoimmune response against the intracellular ribonucleoproteins, SSA/Ro. Most studies confirm and extend previous investigations suggesting that the risk of arrhythmic events is higher in patients with anti-Ro activity targeted to Ro52 component of the antigen. The detection of circulating anti-Ro Abs is relatively frequent in the course of autoimmune diseases, particularly Sjögren's syndrome, and systemic lupus erythematosus, but also in other connective tissue diseases (CTD) including mixed CTD, undifferentiated CTD, polymyositis/dermatomyositis, systemic sclerosis, rheumatoid arthritis (RA) and even primary biliary cirrhosis (Lazzerini P E, et al., Arthritis Rheum. 2004; 50:1248-52; Lazzerini P E, et al., Front Cardiovasc Med. 2016; 3:31; and Bourre-Tessier J, et al., Arthritis Care Res (Hoboken). 2011; 63:1031-7). The functional and molecular basis of the anti-Ro Abs associated QTc prolongation was attributed to a direct block of hERG-K channel at the extracellular loop between S5 and S6 of the pore-forming al subunit of hERG-K channel where homology with Ro antigen has been found (Yue Y, et al., Circulation. 2015; 132:230-40). This homology may explain why anti-Ro Abs recognize and target the hERG-K channel since Ro52 antigen is intracellular and not accessible to circulating Abs. The block of hERG-K channels leads to action potential prolongation at the cardiomyocyte level and results in QT interval prolongation at the surface ECG in an animal model for autoimmune associated QTc prolongation (Yue Y, et al., Circulation. 2015; 132:230-40). Yue Y, et al., Circulation. 2015; 132:230-40 describes the homology between Ro52 antibodies and the hERG-K channel extracellular pore region, and is incorporated by reference in its entirety. Disclosed herein are decoy peptides for anti-Ro antibodies thus preventing these pathogenic antibodies for targeting the hERG-K channel. These decoy peptides (SEQ ID NOs: 1-9 or other fragments of SEQ ID NO: 9) are therapeutic compositions for the management and treatment of QTc prolongation in patients with autoantibodies targeting hERG-K channels.

Compositions

Disclosed herein are compositions, including pharmaceutical compositions comprising decoy peptides or polypeptides capable of inhibiting autoantibodies from binding to a human Ether-à-go-go-Related Gene (hERG) potassium (K) channel extracellular pore region and activating the K channel. Further disclosed herein are compositions comprising a fibronectin type III monobody and a decoy peptide or fragment thereof. Also, disclosed herein are compositions comprising decoy peptides or polypeptides capable of treating or preventing QTc prolongation in a subject. Further, disclosed herein are compositions capable of ameliorating or reducing one or more symptoms of QTc prolongation in a subject. Also disclosed herein are compositions comprising decoy peptides or polypeptides capable of preventing or reducing the risk of ventricular tachycardia in a subject. In some aspects, the subject has an autoimmune disease. In some aspects, the ventricular tachycardia can be Torsades de Pointes.

As used herein, the term "peptide" refers to a linear molecule formed by binding amino acid residues to each other via peptide bonds. As used herein, the term "polypeptide" refers to a polymer of (the same or different) amino acids bound to each other via peptide bonds.

As used herein, the term "decoy peptide or polypeptide" refers to a peptide or polypeptide designed to contain a partial peptide sequence in the hERG-K channel extracellular pore region, and the decoy peptide or polypeptide can block the action of anti-Ro antibodies by binding to the anti-Ro antibodies.

Disclosed herein are decoy peptides or polypeptides that comprise or consist of the amino acid sequence of GNMEQPHMDSRIGWLHNLGDQIGKPYNSSGL (SEQ ID NO: 9), or a fragment thereof. In some aspects, the fragment of SEQ ID NO: 9 can be between 5 and 30 amino acids in length. Disclosed herein are decoy peptides or polypeptides that comprise or consist of the amino acid sequence of GNMEQPHMDSRIGWLHNLGDQIGKPYNSSGL (SEQ ID NO: 9), or a variant thereof. In some aspects, the decoy peptide or polypeptide comprises or consists of the amino acid sequence of GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), or GDQIGKPYNSSGL (SEQ ID NO: 8). In some aspects, the decoy peptide or polypeptide comprises or consists of a fragment of SEQ ID NO: 9. In some aspects, the fragment of SEQ ID NO: 9 can be the amino acid sequence of GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), or GDQIGKPYNSSGL (SEQ ID NO: 8). In some aspects, the decoy peptide or polypeptide comprises or consists of the amino acid sequence of GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), or GDQIGKPYNSSGL (SEQ ID NO: 8) or variants thereof. In some aspects, the decoy peptide or polypeptide, fragment or variant thereof can inhibit the binding of anti-Ro antibodies to a human Ether-à-go-go-Related Gene (hERG) potassium channel extracellular pore region. In some aspects, the decoy peptide or polypeptide, fragment or variant thereof can inhibit the binding of anti-Ro antibodies to a hERG-K channel extracellular pore region by competitive inhibition.

Disclosed herein are decoy peptides or polypeptides that comprise fragments of GNMEQPHMDSRIGWLHNLGDQIGKPYNSSGL (SEQ ID NO: 9). In some aspects, the fragments can comprise a sequence having at least 20%, 30%, 40%, 50%, 60%, 70%, 80%, 90%, 95%, 98%, 99% identity to SEQ ID NO: 9. In some aspects, the fragment retains at least 50%, 75%, 80%, 85%, 90%, 95% or 99% of the biological activity of the reference decoy peptide or polypeptides described herein.

Disclosed herein are variants of the decoy peptides or polypeptides described herein. For example, disclosed are variants of GNMEQPHMDSRIGWLHNLGDQIGKPYNSSGL (SEQ ID NO: 9). In some aspects, the variants can comprise a sequence having at least 20%, 30%, 40%, 50%, 60%, 70%, 80%, 90%, 95%, 98%, 99% identity to SEQ ID NO: 9. In some aspects, the variants retain at least 50%, 75%, 80%, 85%, 90%, 95% or 99% of the biological activity of the reference protein described herein.

Disclosed herein are decoy peptides or polypeptides that comprise variants of GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), or GDQIGKPYNSSGL (SEQ ID NO: 8). In some aspects, the variants can comprise a sequence having at least 20%, 30%, 40%, 50%, 60%, 70%, 80%, 90%, 95%, 98%, 99% identity to SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8. In some aspects, the variants retains at least 50%, 75%, 80%, 85%, 90%, 95% or 99% of the biological activity of the reference protein described herein.

In some aspects, the decoy peptide can be GNMEQPHMDSRI (SEQ ID NO: 1). In some aspects, the decoy peptide can be GWLHNLG (SEQ ID NO: 2). In some aspects, the decoy peptide can be DQIGKPYNSSGL (SEQ ID NO: 3). In some aspects, the decoy peptide can be GNMEQPHMDSRIGWLHNLGDQ (SEQ ID NO: 4). In some aspects, the decoy peptide can be HMDSRIGWLHNLGDQ (SEQ ID NO: 5). In some aspects, the decoy peptide can be IGKPYNSSGL (SEQ ID NO: 6). In some aspects, the decoy peptide can be HNLGDQIGKPYNSSGL (SEQ ID NO: 7). In some aspects, the decoy peptide can be GDQIGKPYNSSGL (SEQ ID NO: 8). In some aspects, the decoy peptide can be NMEQPHMDSRIGWLHNLGDQIGKPYNSSGL (SEQ ID NO: 9).

In some aspects, the decoy peptide can comprise or consist of the sequence GNMEQPHMDSRI (SEQ ID NO: 1). In some aspects, the decoy peptide can comprise or consist of the sequence GWLHNLG (SEQ ID NO: 2). In some aspects, the decoy peptide can comprise or consist of the sequence DQIGKPYNSSGL (SEQ ID NO: 3). In some aspects, the decoy peptide can comprise or consist of the sequence GNMEQPHMDSRIGWLHNLGDQ (SEQ ID NO: 4). In some aspects, the decoy peptide can comprise or consist of the sequence HMDSRIGWLHNLGDQ (SEQ ID NO: 5). In some aspects, the decoy peptide can comprise or consist of the sequence IGKPYNSSGL (SEQ ID NO: 6). In some aspects, the decoy peptide can comprise or consist of the sequence HNLGDQIGKPYNSSGL (SEQ ID NO: 7). In some aspects, the decoy peptide can comprise or consist of the sequence GDQIGKPYNSSGL (SEQ ID NO: 8). In some aspects, the decoy peptide can comprise or consist of the sequence NMEQPHMDSRIGWLHNLGDQIGKPYNSSGL (SEQ ID NO: 9).

The term "competitive inhibition" as used herein with reference to a decoy peptide or polypeptide can refer to an inhibition of the binding of an anti-Ro antibody to the hERG-K channel by binding to the anti-Ro antibodies. In some aspects, the decoy peptides or polypeptides disclosed herein can bind to the anti-Ro antibodies and as such that it competes with the hERG-K channel extracellular pore region.

In some aspects, the decoy peptide or polypeptide can be of any length so long as the binding of the anti-Ro antibodies to the hERG-K channel extracellular pore region is blocked or inhibited.

In some aspects, the anti-Ro antibodies can be anti-Ro52 (52 kD) or anti-Ro60 (60 kD). In some aspects, the anti-Ro antibodies can be anti-Ro52 antibodies. In some aspects, the anti-Ro antibodies can be anti-Ro 60 antibodies.

In some aspects, the decoy peptides or polypeptides described herein can further comprise 1, 2, 3, 4, 5, 10, 15, 20, 25, 30, 35, 40, 45, 50 amino acid residues at the N-terminal end of the disclosed decoy peptides or polypeptides. In some aspects, the decoy peptides or polypeptides described herein can further comprise 1, 2, 3, 4, 5, 10, 15, 20, 25, 30, 35, 40, 45, 50 amino acid residues at the C-terminal end of the disclosed decoy peptides or polypeptides disclosed herein. In some aspects, the amino acid residues that can be present at either the N-terminal end or the C-terminal end of any of the decoy peptides or polypeptides disclosed herein can be unimportant for inhibiting the binding of the anti-Ro antibodies which bind to the hERG-K channel extracellular pore region. In some aspects, the amino acid residues added to the N-terminal end or the C-terminal end of the decoy peptides or polypeptides disclosed herein may prevent ubiquitination, improve stability, help maintain the three dimensional structure of the peptide, or a combination thereof.

In some aspects, the decoy peptides or polypeptides disclosed herein can further comprise a peptide or polypeptide having one or more amino acid residues with a modified side chain. In some aspects, one or more amino acids of any of the decoy peptides or polypeptides disclosed here can have a modified side chain. Examples of side chain modifications include but are not limited to modifications of amino acid groups, such as reductive alkylation; amidination with methylacetimidate; acylation with acetic anhydride; carbamolyation of amino groups with cynate; trinitrobenzylation of amino acid with 2,4,6-trinitrobenzene sulfonic acid (TNBS); alkylation of amino groups with succinic anhydride; and pyridoxylation with pridoxal-5-phosphate followed by reduction with $NaBH_4$.

In some aspects, the guanidine group of the arginine residue may be modified by the formation of a heterocyclic condensate using a reagent, such as 2,3-butanedione, phenylglyoxal, and glyoxal. In some aspects, the carboxyl group may be modified by carbodiimide activation via O-acylisourea formation, followed by subsequent derivatization, for example, to a corresponding amide.

In some aspects, the sulfhydryl group may be modified by methods, such as carboxymethylation with iodoacetic acid or iodoacetamide; performic acid oxidation with cysteic acid; formation of mixed disulfides by other thiol compounds; a reaction by maleimide, maleic anhydride, or other substituted maleimide; formation of mercury derivatives using 4-chloromercuribenzoate, 4-chloromercuriphenylsulfonic acid, phenylmercury chloride, 2-chloromercuri-4-nitrophenol, and other mercurial agents; and carbamolyation with cyanate at alkaline pH. In addition, the sulfhydryl group of cysteine may be substituted with a selenium equivalent, whereby a diselenium bond may be formed instead of at least one disulfide bonding site in the peptide.

In some aspects, the tryptophan residue may be modified by, for example, oxidation with N-bromosuccinimide or alkylation of the indole ring by 2-hydroxy-5-nitrobenzyl bromide or sulfonyl halide. Meanwhile, the tyrosine residue may be modified by nitration using tetranitromethane to form a 3-nitrotyrosine derivative.

In some aspects, the modification of the imidazole ring of the histidine residue may be accomplished by alkylation with an iodoacetic acid derivative or N-carbethoxylation with diethylpyrocarbonate.

In some aspects, the proline residue may be modified by, for example, hydroxylation at the 4-position.

In some aspects, the decoy peptides or polypeptides described herein can be further modified to improve stability. In some aspects, any of the amino acid residues of the decoy peptides or polypeptides described herein can be modified to improve stability. In some aspects, decoy peptide or polypeptide can have at least one amino acid residue that has an acetyl group, a fluorenylmethoxy carbonyl group, a formyl group, a palmitoyl group, a myristyl group, a stearyl group, or polyethylene glycol. In some aspects, an acetyl protective group can be bound to the decoy peptide or polypeptide described herein.

As used herein, the term "stability" refers to storage stability (e.g., room-temperature stability) as well as in vivo stability. The foregoing protective group can protect the decoy peptides or polypeptides described herein from the attack of protein cleavage enzymes in vivo.

As used herein, the term "decoy peptide or polypeptide" can also be used to include functional equivalents of the decoy peptides or polypeptides described herein. As used herein, the term "functional equivalents" can refer to amino acid sequence variants having an amino acid substitution, addition, or deletion in some of the amino acid sequence of the decoy peptide or polypeptide while simultaneously having similar or improved biological activity, compared with the decoy peptide or polypeptide as described herein. In some aspects, the amino acid substitution can be a conservative substitution. Examples of the naturally occurring amino acid conservative substitution include, for example, aliphatic amino acids (Gly, Ala, and Pro), hydrophobic amino acids (Ile, Leu, and Val), aromatic amino acids (Phe, Tyr, and Trp), acidic amino acids (Asp and Glu), basic amino acids (His, Lys, Arg, Gln, and Asn), and sulfur-containing amino acids (Cys and Met). In some aspects, the amino acid deletion can be located in a region that is not directly involved in the activity of the decoy peptide and polypeptide disclosed herein.

In some aspects, the amino acid sequence of the decoy peptides or polypeptides described herein can include a peptide sequence that has substantial identity to any of sequence of the decoy peptides or polypeptides disclosed herein. As used herein, the term "substantial identity" means that two amino acid sequences, when optimally aligned and then analyzed by an algorithm normally used in the art, such as BLAST, GAP, or BESTFIT, or by visual inspection, share at least about 60%, 70%, 80%, 85%, 90%, or 95% sequence identity. Methods of alignment for sequence comparison are known in the art.

In some aspects, the amino acid sequence of the decoy peptides or polypeptides described herein can include a peptide sequence that has some degree of identity or homology to any of sequences of the decoy peptides or polypeptides disclosed herein. The degree of identity can vary and be determined by methods known to one of ordinary skill in the art. The terms "homology" and "identity" each refer to sequence similarity between two polypeptide sequences. Homology and identity can each be determined by comparing a position in each sequence which can be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. The decoy peptides or polypeptides described herein can have at least or about 25%, 50%, 65%, 75%, 80%, 85%, 90%, 95%, 96%, 97%, 98%, or 99% identity or homology to the decoy peptide or polypeptide, wherein the decoy peptide or polypeptide is one or more of SEQ ID NOs: 1-9.

Disclosed herein are compositions comprising a fibronectin type III (Fn3) monobody and decoy peptide comprising or consisting of the sequence GNMEQPHMDSRIGWLHNLGDQIGKPYNSSGL (SEQ ID NO: 9), or a fragment thereof. Disclosed herein are compositions comprising a fibronectin type III (Fn3) monobody and a one or more of the decoy peptides disclosed herein. In some aspects, the Fn3 monobody can be conjugated to the decoy peptide or fragment thereof. In some aspects, the decoy peptide or fragment thereof can be conjugated to the C-terminus of the Fn3 monobody. In some aspects, the decoy peptide or fragment thereof can be conjugated to the N-terminus of the Fn3 monobody. In some aspects, the Fn3 monobody conjugated to the decoy peptide or fragment thereof does not destabilize the decoy peptide or fragment thereof. In some aspects, the decoy peptide comprises or consists of the sequence GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), or GDQIGKPYNSSGL (SEQ ID NO: 8). In some aspects, the decoy peptide comprises or consists of the sequence GNMEQPHMDSRIGWLHNLGDQ (SEQ ID NO: 4).

In some aspects, the Fn3 monobody conjugated to any of the decoy peptides or fragments thereof allows for a 3D conformation of the polypeptide (vs linear) such that it is more effective in neutralizing the pathogenic anti-Ro antibodies, thereby resulting in a normalization of the QTc and thus preventing the occurrence of the associated fatal polymorphic ventricular tachycardia (arrhythmia) and sudden cardiac death. As described herein as an example, the Fn3 monobody conjugated, for instance to SEQ ID NO: 4 shows that this polypeptide can last longer in the circulation with two injections between day 16 to day 31 (lasted at least 15 days while the QTc is still within the normal values, see, FIG. 5). The clinical translation is that there will be no need for daily administration of the decoy peptide but rather a once per week administration of the Fn3 monobody conjugated to the decoy peptide or fragment thereof.

In some aspects, the decoy peptides or polypeptides described herein can be part of a scaffold protein. In some aspects, the scaffold for formation of a polypeptide monobody can be any polypeptide monobody. In some aspects, the polypeptide monobody can be covalently attached to any of the decoy peptides disclosed herein or fragments thereof. In some aspects, decoy peptide or fragment thereof can be a part of the same amino acid chain backbone in tandem with the Fn3 domain. In some aspects, the polypeptide monobody does not have a disulfide bond. In some aspects, the polypeptide monobody that is conjugated to the decoy peptide or fragment thereof does not destabilize the decoy peptide or fragment thereof. In some aspects, the scaffold for formation of a polypeptide monobody can be the fibronectin type III (Fn3) domain. The characteristics of the underlying Fn3 scaffold of a fibronectin type III (Fn3) monobody can be small (~90 residues), stable, easy to produce. As used herein, "polypeptide monobody" or "monobody" refers to polypeptide which includes a beta-strand domain lacking in disulfide bonds and containing a plurality of beta-strands, two or more loop regions each connecting one beta-strand to another beta-strand, and optionally an N-terminal tail, a C-terminal tail, or both. In some aspects, at least one of the two or more loop regions, the N-terminal tail, or the C-terminal tail may naturally or may be designed to have activity in binding a target protein or molecule. In some aspects, such polypeptide monobodies can include three or more loop regions or, even more specifically, four or more loop regions. The size of such polypeptide monobodies is preferably less than about 30 kDa, more preferably less than about 20 kDa.

Fibronectin is a large protein which plays important roles in the formation of extracellular matrix and cell-cell interactions; it consists of many repeats of three types (types I, II, and III) of small domains (Baron et al., 1991). Fn3 itself is the paradigm of a large subfamily (Fn3 family or s-type Ig family) of the immunoglobulin superfamily. The Fn3 family includes cell adhesion molecules, cell surface hormone and cytokine receptors, chaperoning, and carbohydrate-binding domains (for reviews, see Bork & Doolittle, 1992; Jones, 1993; Bork et al., 1994; Campbell &

Spitzfaden, 1994; Harpez & Chothia, 1994). Fibronectin is a ligand of integrins, and it contains repeats of three types of domains. In some aspects, the Fn3 domain can be the tenth fibronectin type III domain (FNfn10). FNfn10 includes the RGD sequence in the loop connecting the F and G beta-strands (FG loop) (Main et al., 1992). In some aspects, the FNfn10 can be referred to as a monobody (Batori, V., et al. (2002) Exploring the potential of the monobody scaffold: effects of loop elongation on the stability of a fibronectin type III domain, Protein Eng 15:1015-1020). FNfn10 is structurally similar to an antibody heavy chain.

FNfn10 was developed as a scaffold for phage display of peptides because of its small size (94 residues), monomeric assembly, and ability to retain its global fold while exposed loops were randomized (Koide et al., 1998). In addition, FNfn10 lacks cysteine residues and requires no post-translational modification, allowing for large-scale bacterial expression. It has been shown that residues in the FG loop including the RGD sequence are highly flexible (Main et al., 1992; Carr et al., 1997) and this flexibility of the FG loop has been implicated as the origin of the ability of FNfn10 to interact with multiple integrins (Main et al., 1992).

Crystallographic studies have revealed that the structure of the DNA binding domains of the transcription factor NF-kB is also closely related to the Fn3 fold (Ghosh et al., 1995; Muller et al., 1995). These proteins are involved in specific molecular recognition, and in most cases ligand-binding sites are formed by surface loops, suggesting that the Fn3 scaffold is an excellent framework for building specific binding proteins. The 3D structure of Fn3 has been determined by NMR (Main et al., 1992) and by X-ray crystallography (Leahy et al., 1992; Dickinson et al., 1994). The structure is best described as a beta-sandwich similar to that of antibody VH domain except that Fn3 has seven beta-strands instead of nine. There are three loops on each end of Fn3; the positions of the BC, DE, and FG loops approximately correspond to those of CDR 1, 2 and 3 of the VH domain.

A fibronectin type III (Fn3) monobody lacks binding sites for metal ions and the central disulfide bond. In some aspects, the Fn3 scaffold of the fibronectin type III (Fn3) monobody can be diversified. For example, the Fn3 scaffold of the fibronectin type III (Fn3) monobody can comprise one or more modifications to the loops BC (between the second and third beta sheets), DE (between the fourth and fifth beta sheets) and FG (between the sixth and seventh sheets). Such a design can create diversified positions on a convex surface that is suitable for targeting concave surfaces such as enzyme active sites. In some aspects, the Fn3 scaffold of the fibronectin type III (Fn3) monobody can comprise one or more modifications to in one or more of the C, D, F and G (or the 3rd, 4th, 6th and 7th) strands in addition to the CD and FG loops. Such a design can create a flatter, slightly concave surface that is suitable for targeting surfaces typically involved in protein-protein interactions.

Fn3 is small (about 94 residues), monomeric, soluble, and stable. It has a molecular mass of about 10 kDa, fifteen times smaller than an IgG type antibody and comparable to the size of a single variable domain of an antibody. It is one of few members of IgSF that do not have disulfide bonds and, therefore, is stable under reducing conditions. Fn3 has been expressed in *E. Coli* (Aukhil et al., 1993). In addition, 17 Fn3 domains are present just in human fibronectin, providing important information on conserved residues which are often important for the stability and folding (see Main et al., 1992; Dickinson et al., 1994). From sequence analysis, large variations are seen in the BC and FG loops, suggesting that the loops are not important to stability. NMR studies have revealed that the FG loop is highly flexible; the flexibility has been implicated for the specific binding of the 10th Fn3 to $\alpha 5\beta 1$ integrin through the Arg-Gly-Asp (RGD) motif in the crystal structure of human growth hormone-receptor complex (de Vos et al., 1992), the second Fn3 domain of the receptor interacts with growth hormone via the FG and BC loops, suggesting it is feasible to build a binding site using the two loops.

The tenth type III module of fibronectin has a fold similar to that of immunoglobulin domains, with seven beta strands forming two antiparallel beta sheets, which pack against each other (FIG. 1; Main et al., 1992). The structure of the type H module includes seven beta strands, which form a sandwich of two antiparallel sheets, one containing three strands (ABE) and the other four strands (C'CFG) (Williams & Barclay, 1988). The beta sheet contains residues Glu-9-Thr-14 (A), Ser-17-Asp-23 (B), and Thr-56-Ser-60 (E). The majority of the conserved residues contribute to the hydrophobic core, with the invariant hydrophobic residues Trp-22 and Try-68 lying toward the N-terminal and C-terminal ends of the core, respectively. The beta strands are much less flexible and appear to provide a rigid framework upon which functional, flexible loops can be built. The topology is similar to that of immunoglobulin C domains.

In some aspects, the polypeptide monobodies can be fibronectin type III (Fn3)-derived polypeptide monobodies. Fn3 monobodies include at least two Fn3 beta-strand domain sequences with a loop region sequence linked between adjacent beta-strand domain sequences and optionally, an N-terminal tail of at least about 2 amino acids, a C-terminal tail of at least about 2 amino acids, or both. The loop region sequence, the N-terminal tail, or the C-terminal tail, or combinations thereof include an amino acid sequence which has binding specificity for $\alpha 5\beta 3$ integrin. To render a loop region sequence, N-terminal tail, or C-terminal tail capable of binding to $\alpha 5\beta 3$ integrin, either the loop region sequence, the N-terminal tail, the C-terminal tail, or a combination thereof varies by deletion, insertion, or replacement of at least two amino acids from a corresponding loop region, N-terminal tail, or C-terminal tail in a wild-type or mutant Fn3 scaffold.

In some aspects, the wild-type Fn3 monobody or scaffold can be the tenth Fn3 domain of human fibronectin (FNfn10), which has an amino acid sequence according to SEQ ID NO: 11: VSDVPTDLEVVAATPTSLLISWDAPAVTVRYYRIT YGETGGNSPVQEFTVPGSKSTATISGLKPGVDYTITV-YAVTGRGDSPASSKPISINYRT. In some aspects, the Fn3 monobody can be a mutant Fn3 monobody. In some aspects, the mutant Fn3 monobody can be the tenth Fn3 domain of human fibronectin which has a modified Asp7, which is replaced by a non-negatively charged amino acid residue (e.g., Asn, Lys, etc.). As reported in Koide et al. (2001), both of these mutations have the effect of promoting greater stability of the mutant FNfn10 at neutral pH as compared to the wild-type FNfn10.

Pharmaceutical Compositions

As disclosed herein, are pharmaceutical compositions, comprising one or more of the decoy peptides or polypeptides or one or more of the compositions described herein. Also disclosed herein, are pharmaceutical compositions, comprising one or more of the decoy peptides or polypeptides or one or more of the compositions described herein and a pharmaceutical acceptable carrier. Further disclosed herein are pharmaceutical compositions for treating or preventing QTc prolongation; ameliorating or reducing one or more symptoms of QTc prolongation; and preventing or reducing the risk of ventricular tachycardia in a subject. In some aspects, the pharmaceutical compositions can comprise: a) a therapeutically effective amount of one or more of the decoy peptides or polypeptides or one or more of the compositions described herein; and b) a pharmaceutically acceptable carrier. In some aspects, the decoy peptides described herein can inhibit the binding of anti-Ro antibodies to a hERG-K channel extracellular pore region. In some aspects, the decoy peptides described herein can inhibit the binding of anti-Ro antibodies to a hERG-K channel extracellular pore region by competitive inhibition.

The pharmaceutical compositions described above can be formulated to include a therapeutically effective amount of a decoy peptide or polypeptide or a pharmaceutical acceptable carrier. Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to QTc prolongation or ventricular tachycardia.

The pharmaceutical compositions described herein can be administered to the subject (e.g., a human patient) in an amount sufficient to delay, reduce, or preferably prevent the onset of clinical disease. Accordingly, in some aspects, the patient can be a human patient. In therapeutic applications, compositions can be administered to a subject (e.g., a human patient) already with or diagnosed with an autoimmune disease in an amount sufficient to at least partially improve a sign or symptom or to inhibit the progression of (and preferably reverse or arrest) the symptoms of the condition, its complications, and consequences (e.g., developing QTc prolongation or ventricular tachycardia). An amount adequate to accomplish this is defined as a "therapeutically effective amount." A therapeutically effective amount of a pharmaceutical composition can be an amount that achieves a cure, but that outcome is only one among several that can be achieved. As noted, a therapeutically effect amount includes amounts that provide a treatment in which the onset or progression of QTc prolongation or ventricular tachycardia or a symptom of QTc prolongation or ventricular tachycardia is ameliorated, prevented, treated, or managed. One or more of the symptoms can be less severe. Recovery can be accelerated in an individual who has been treated.

In some aspects, the pharmaceutical composition can be formulated for intravenous administration. In some aspects, the pharmaceutical composition can be formulated for subcutaneous, intranasal or oral administration. The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used to deliver the decoy peptide. Thus, compositions can be prepared for parenteral administration that includes the decoy peptides or polypeptides dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

Methods of Treatment

Disclosed herein are methods of treating corrected QT (QTc) prolongation in a subject. In some aspects, the QTc prolongation can be associated with an autoimmune disease. In some aspects, the methods can comprise: administering to a subject a therapeutically effective amount of one or more decoy peptides or polypeptides or one or more of the compositions disclosed herein. In some aspects, the methods can further comprise: administering to a subject a therapeutically effective amount of one or more decoy peptides or polypeptides or one or more of the compositions with or in a pharmaceutically acceptable carrier.

The QT interval is a measurement made on an electrocardiogram used to assess some of the electrical properties of the heart. It is calculated as the time from the start of the Q wave to the end of the T wave, and approximates to the time taken from when the cardiac ventricles start to contract to when they finish relaxing. An abnormally long or abnormally short QT interval is associated with an increased risk of developing abnormal heart rhythms and sudden cardiac death. Abnormalities in the QT interval can be caused by genetic conditions such as long QT syndrome, or acquired by certain medications, by electrolyte imbalances within the blood such as hypokalaemia, hypocalcemia and hypomagnesemia or by hormonal imbalances such as hypothyroidism. Other causes of acquired long QT syndrome include but are not limited to structural heart diseases, bradyarrhythmias, endocrine and liver diseases, nervous system injuries, starvation, hypothermia, and toxins. Examples of QT-prolonging risk factors include but are not limited to both acquired (e.g., inflammation, autoimmunity, human immunodeficiency virus infection, male hypogonadism, heart failure with preserved ejection fraction, and QT-prolonging drinks) and genetic (e.g., polygenic mutations) conditions. The QT interval changes in response to the heart rate; as heart rate increases, the QT interval shortens.

Prolonged QTc predisposes to premature electrical activity during the early or late phases of repolarization. This increases the risk of developing ventricular arrhythmias, including fatal ventricular fibrillation. Higher rates of prolonged QTc are seen in females and older patients. It is widely accepted that the cut-off values for QTc prolongation are gender-related (>470 ms for men, >480 ms for women). Prolonged QTc is also associated with ECG findings called Torsades de Pointes, which are known to degenerate into ventricular fibrillation, and sudden cardiac death. If ventricular arrhythmia occurs as a result of prolonged QTc, some symptoms may include chest fluttering (palpitations), shortness of breath or chest pain, lightheadedness, near fainting or fainting and cardiac arrest.

Disclosed herein are methods of preventing corrected QT (QTc) prolongation in a subject. In some aspects, the methods can comprise: administering to a subject a therapeutically effective amount of one or more decoy peptides or polypeptides or one or more of the compositions disclosed herein. In some aspects, the methods can further comprise administering to a subject a therapeutically effective amount of one or more decoy peptides or polypeptides or one or more of the compositions with or in a pharmaceutically acceptable carrier.

Disclosed herein are methods of ameliorating one or more symptoms of corrected QT (QTc) prolongation in a subject. In some aspects, the methods can comprise: a) administering to a subject a therapeutically effective amount of one or more decoy peptides or polypeptides or one or more of the compositions disclosed herein. In some aspects, the methods can further comprise administering to a subject a therapeutically effective amount of one or more decoy peptides or polypeptides or one or more of the compositions with or in a pharmaceutically acceptable carrier.

Disclosed herein are methods of preventing one or more symptoms of corrected QT (QTc) prolongation in a subject. In some aspects, the methods can comprise: a) administering to a subject a therapeutically effective amount of one or more decoy peptides or polypeptides or one or more of the compositions disclosed herein. In some aspects, the methods can further comprise administering to a subject a therapeutically effective amount of one or more decoy peptides or polypeptides or one or more of the compositions with or in a pharmaceutically acceptable carrier.

Disclosed herein are methods of reducing the risk of ventricular tachycardia in a subject. In some aspects, the methods can comprise: administering to a subject a therapeutically effective amount of one or more decoy peptides or polypeptides or one or more of the compositions disclosed herein. In some aspects, the methods can further comprise administering to a subject a therapeutically effective amount of one or more decoy peptides or polypeptides or one or more of the compositions with or in a pharmaceutically acceptable carrier.

Disclosed herein are methods of preventing the risk of ventricular tachycardia in a subject. In some aspects, the methods can comprise: administering to a subject a therapeutically effective amount of one or more decoy peptides or polypeptides or one or more of the compositions disclosed herein. In some aspects, the methods can further comprise administering to a subject a therapeutically effective amount of one or more decoy peptides or polypeptides or one or more of the compositions with or in a pharmaceutically acceptable carrier.

Disclosed herein are methods of competitively inhibiting the binding of anti-Ro antibodies to the hERG potassium channel extracellular pore region. In some aspects, the methods can comprise: administering to a subject a therapeutically effective amount of one or more decoy peptides or polypeptides or one or more of the compositions disclosed herein to subject. In some aspects, the methods can further comprise administering to a subject a therapeutically effective amount of one or more decoy peptides or polypeptides or one or more of the compositions with or in a pharmaceutically acceptable carrier.

Disclosed herein are methods of treating corrected QT (QTc) prolongation. In some aspects, the methods can comprise: administering to a subject with QTc prolongation a therapeutically effective amount of a decoy peptide comprising or consisting of the amino acid sequence of GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), GDQIGKPYNSSGL (SEQ ID NO: 8), GNMEQPHMDSRIGWLHNLG DQIGKPYNSSGL (SEQ ID NO: 9), or a fragment of SEQ ID NO: 9. In some aspects, the methods can comprise: administering to a subject with QTc prolongation a therapeutically effective amount of any of the decoy peptides disclosed herein or any of the compositions or pharmaceutical compositions disclosed herein.

Disclosed herein are methods of preventing corrected QT (QTc) prolongation. In some aspects, the methods can comprise: administering to a subject a therapeutically effective amount of a decoy peptide comprising or consisting of the amino acid sequence of GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), GDQIGKPYNSSGL (SEQ ID NO: 8), GNMEQPHMDSRIGWLHNLG DQIGKPYNSSGL (SEQ ID NO: 9), or a fragment of SEQ ID NO: 9. In some aspects, the methods can comprise: administering to a subject with QTc prolongation a therapeutically effective amount of any of the decoy peptides disclosed herein or any of the compositions or pharmaceutical compositions disclosed herein.

Disclosed herein are methods of ameliorating one or more symptoms of corrected QT (QTc) prolongation. In some aspects, the methods can comprise: administering to a subject a therapeutically effective amount of a decoy peptide comprising or consisting of the amino acid sequence of GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), GDQIGKPYNSSGL (SEQ ID NO: 8), GNMEQPHMDSRIGWLHNLG DQIGKPYNSSGL (SEQ ID NO: 9), or a fragment of SEQ ID NO: 9. In some aspects, the methods can comprise: administering to a subject with QTc prolongation a therapeutically effective amount of any of the decoy peptides disclosed herein or any of the compositions or pharmaceutical compositions disclosed herein.

Disclosed herein are methods of reducing the risk of ventricular tachycardia. In some aspects, the methods can comprise: administering to a subject a therapeutically effective amount of a decoy peptide comprising or consisting of the amino acid sequence of GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), GDQIGKPYNSSGL (SEQ ID NO: 8), GNMEQPHMDSRIGWLHNLG DQIGKPYNSSGL (SEQ ID NO: 9), or a fragment of SEQ ID NO: 9. In some aspects, the methods can comprise: administering to a subject with QTc prolongation a therapeutically effective amount of any of the decoy peptides disclosed herein or any of the compositions or pharmaceutical compositions disclosed herein.

Also disclosed herein are methods of monitoring risk of corrected QT (QTc) prolongation and treating the QTc prolongation in a subject. In some aspects, the methods can comprise: a) measuring the level of anti-Ro antibodies in a sample from the subject; b) comparing the level of anti-Ro antibodies in the sample of step a) with a control or reference sample; c) determining that the risk of QTc prolongation is increased if the level of anti-Ro antibodies in step b) is increased when compared to the level of binding in the control or reference sample; and d) administering to the subject a therapeutically effective amount of any of the decoy peptides or polypeptides described herein or any of the compositions or pharmaceutical compositions described herein. In some aspects, the method can also include the step of obtaining a sample from the subject. In some aspects, the sample can comprise one or more anti-Ro antibodies. In some aspects, the subject can have an autoimmune disease. In some aspects, the sample can be blood, plasma or serum. In some aspects, the anti-Ro antibodies in the sample from the subject can be caused by an autoimmune disease. In some aspects, the autoimmune disease can be Sjorgren's syndrome, systemic lupus erythematosus, mixed connective tissue disease, undifferentiated connective tissue disease, polymyositis, dermatomyositis, systemic sclerosis, rheumatoid arthritis, or primary biliary cirrhosis. In some aspects, the subject can have hypokalemia or hypomagnesemia. In some aspects, the methods can further comprise monitoring the level of anti-Ro antibodies. In some aspects, the decoy peptide can inhibit the binding of anti-Ro antibodies to a hERG potassium channel extracellular pore region. In some aspects, the decoy peptide can inhibit the binding of anti-Ro antibodies to a hERG potassium channel extracellular pore region by competitive inhibition or by neutralizing the anti-Ro antibodies. In some aspects, the subject can be identified in need of treatment before the administration step. In some aspects, the subject can be human.

In some aspects, the methods can comprise administering a composition that can be formulated for intravenous, subcutaneous, intranasal or oral administration.

In some aspects, the level of binding of the anti-Ro antibodies in the sample can be increased or higher when compared to the level of binding of anti-Ro antibodies in a control or reference sample. In some aspects, a sample from a subject can be identified as being in need of treatment when the level of binding of the anti-Ro antibodies in the sample can be increased or higher when compared to the level of binding of anti-Ro antibodies in a control or reference sample. In some aspects, the sample from the subject can be identified as being at risk for a QTc prolongation or ventricular tachycardia. In some aspects, the control or reference sample can be from an age-matched sample.

In some aspects, the level of binding of the anti-Ro antibodies can be determined by various analysis methods. For example, the binding of anti-Ro antibodies can be determined in various immunoassay formats. These immunological analysis methods may be carried out according to various quantitative immunoassay protocols that have been developed in the prior art. Examples of the immunoassay format include radioactive immunoassay, radioactive immunoprecipitation, immunoprecipitation, enzyme-linked immunosorbent assay (ELISA), captured-ELISA, inhibition or competition analysis, sandwich assay, immunofluorescent staining, and immunoaffinity purification, but are not limited thereto.

Disclosed herein are methods of competitively inhibiting the binding of anti-Ro antibodies to a hERG potassium channel extracellular pore region. In some aspects, the method can comprise: administering to a subject a therapeutically effective amount of a decoy peptide comprising or consisting of the amino acid sequence of GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), GDQIGKPYNSSGL (SEQ ID NO: 8), GNMEQPHMDSRIGWLHNLG DQIGKPYNSSGL (SEQ ID NO: 9), or a fragment of SEQ ID NO: 9. In some aspects, the method can comprise: administering to a subject a therapeutically effective amount of a decoy peptide comprising or consisting of a variant of the amino acid sequence of GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), GDQIGKPYNSSGL (SEQ ID NO: 8), GNMEQPHMDSRIGWLHNLG DQIGKPYNSSGL (SEQ ID NO: 9), or a fragment thereof. In some aspects, the subject can be identified in need of treatment before the administration step. In some aspects, the subject can be human. In some aspects, the subject can be at risk for developing QTc prolongation or ventricular tachycardia. In some aspects, the subject has an autoimmune disease. In some aspects, the autoimmune disease can be Sjorgren's syndrome, systemic lupus erythematosus, mixed connective tissue disease, undifferentiated connective tissue disease, polymyositis, dermatomyositis, systemic sclerosis, rheumatoid arthritis, or primary biliary cirrhosis.

Disclosed herein are methods of competitively inhibiting the binding of anti-Ro antibodies to a hERG potassium channel extracellular pore region. In some aspects, the method can comprise: administering to a subject a therapeutically effective amount of any of decoy peptide or polypeptides disclosed herein. In some aspects, the methods can comprise: administering to a subject a therapeutically effective amount of any of the compositions disclosed herein. In some aspects, the subject can be identified in need of treatment before the administration step. In some aspects, the subject can be human. In some aspects, the subject can be at risk for developing QTc prolongation or ventricular tachycardia. In some aspects, the subject has an autoimmune disease. In some aspects, the autoimmune disease can be Sjorgren's syndrome, systemic lupus erythematosus, mixed connective tissue disease, undifferentiated connective tissue disease, polymyositis, dermatomyositis, systemic sclerosis, rheumatoid arthritis, or primary biliary cirrhosis.

In some aspects, the subject can be identified as being in need of treatment before the administration step. In some aspects, the subject can have an autoimmune disease. In some aspects, the subject can carry anti-Ro antibodies. In some aspects, the anti-Ro antibodies are detectable in a subject's blood. In some aspects, the methods can further comprise monitoring the status of the anti-Ro antibodies. In some aspects, methods can further comprise monitoring the status of the anti-Ro antibodies to determine whether to continue administering any of the decoy peptides or polypeptides or fragments thereof, or compositions or pharmaceutical compositions described herein.

In some aspects, the autoimmune disease can be Sjorgren's syndrome, systemic lupus erythematosus, mixed connective tissue disease, undifferentiated connective tissue disease, polymyositis, dermatomyositis, systemic sclerosis, rheumatoid arthritis, primary biliary cirrhosis or a combination thereof.

In some aspects, the subject can have hypokalemia or hypomagnesemia. In some aspects, the subject can have an imbalance of one or more electrolytes. In some aspects, the subject can have a drug-induced QTc prolongation, one or more genetic factors causing long QT syndrome, an organic cardiac diseases, or a combination thereof. In some aspects, the subject can be a female. Examples of drugs that can induce QTc prolongation can be found at crediblemeds.org/index.php/login/dlcheck. In some aspects, the drug can be an anti-depressants (e.g., amitriptyline, imipramine, citalopram, amitriptyline); an antipsychotics (e.g., haloperidol, ziprasidone, quetiapine, thioridazine, olanzapine, risperidone); an antibiotic (e.g., Macrolides, fluoroquinolones); and an anti-arrhythmic (e.g., amiodarone, sotalol, dofetilide, procainamide, quinidine, flecainide). Examples of organic cardiac diseases or cardiac diseases include but is not limited to left ventricular hypertrophy, heart failure, myocardial ischemia, hypertension, diabetes mellitus, increased thyroid hormone concentrations, elevated serum cholesterol, high body mass index, and electrolyte abnormalities (including hypokalemia and hypomagnesaemia). Genetic (congenital) factors are associated with causing long QT syndrome. Over 17 types of congenital long QT syndrome have been identified. Examples of the most common types of genetic long QT syndrome include but are not limited to LQT1 (KCNQ1, accounts for 30-35% of long QT syndrome), LQT2 (KCNH2, 20-25%) and LQT3 (SCNSA, 5-10%).

Amounts effective for this use can depend on the severity of the condition, disease or disorder or the severity of the risk of the condition, disease or disorder, and the weight and general state and health of the subject, but generally range from about 0.05 µg to about 1000 µg (e.g., 0.5-100 µg) of an equivalent amount of the decoy peptide per dose per subject. Suitable regimes for initial administration and booster administrations are typified by an initial administration followed by repeated doses at one or more hourly, daily, weekly, or monthly intervals by a subsequent administration. For example, a subject can receive decoy peptide or polypeptide in the range of about 0.05 to 1,000 µg equivalent dose per dose one or more times per week (e.g., 2, 3, 4, 5, 6, or 7 or more times per week). For example, a subject can receive 0.1 to 2,500 µg (e.g., 2,000, 1,500, 1,000, 500, 100, 10, 1, 0.5, or 0.1 µg) dose per week. In some aspects, a subject can receive one dose of any of the decoy peptides or polypeptides or any of the compositions or pharmaceutical compositions disclosed herein once per week. A subject can also receive decoy peptide or polypeptide in the range of 0.1 to 3,000 µg per dose once every two or three weeks. A subject can also receive 2 mg/kg every week (with the weight calculated based on the weight of the decoy peptide or polypeptide.

The total effective amount of decoy peptide or polypeptide in the compositions or pharmaceutical compositions disclosed herein can be administered to a mammal as a single dose, either as a bolus or by infusion over a relatively short period of time, or can be administered using a fractionated treatment protocol in which multiple doses are administered over a more prolonged period of time (e.g., a dose every 4-6, 8-12, 14-16, or 18-24 hours, or every 2-4 days, 1-2 weeks, or once a month). In some aspects, any of the compositions disclosed herein can be administered once per week. Alternatively, continuous intravenous infusions sufficient to maintain therapeutically effective concentrations in the blood are also within the scope of the present disclosure.

The therapeutically effective amount of one or more of the decoy peptides or polypeptides present within the compositions described herein and used in the methods as disclosed herein applied to mammals (e.g., humans) can be determined by one of ordinary skill in the art with consideration of individual differences in age, weight, and other general conditions (as described herein).

EXAMPLES

Example 1: Compositions of Matter for Preventing and Treating Autoimmune Associated Cardiac Arrhythmogenesis Described herein are experiments and the design of a biologic therapy for the pathogenic anti-Ro52 antibodies (Abs)-elicited phenotype of abnormal QTc prolongation on the surface electrocardiogram (ECG) and related ventricular arrhythmias in adult patients with autoimmune diseases. Short biologic peptides were designed and tested in vivo to test their function as decoys for the circulating pathogenic anti-Ro antibodies found in patients with autoimmune diseases. These decoy peptides can prevent these Abs from targeting the hERG-K channel responsible for cardiac repolarization and QT interval on ECG and thus representing an alternative therapeutic approach for the prevention and treatment of QTc prolongation and related fatal arrhythmias in patients with autoantibodies targeting hERG-K channels. By developing and testing short decoy peptides on the reversal of QTc prolongation in a guinea-pig animal model, the most effective decoy peptide can then be characterized in preclinical animal studies and subsequently in clinical trials. This approach will have significant therapeutic implications for patients with autoimmune diseases.

Several short peptides (Table 1) were designed. These peptides mimic portions of the hERG-K channel extracellular pore regions of the channel and thus serve as a bate (decoy) for pathogenic circulating antibodies (FIG. 1). Table 1 shows the amino acid sequences of the short linear peptides (peptide 1 to peptide 8), the E-pore peptide, and the scrambled control peptide designed from the extracellular loop between S5 and S6 (E-pore peptide) of the hERG-K channel.

TABLE 1

Amino acid sequences.

| SEQ ID NO: | Sequence | Name |
| --- | --- | --- |
| 1 | GNMEQPHMDSRI | Peptide 1 |
| 2 | GWLHNLG | Peptide 2 |
| 3 | DQIGKPYNSSGL | Peptide 3 |
| 4 | GNMEQPHMDSRIGWLHNLGDQ | Peptide 4 |
| 5 | HMDSRIGWLHNLGDQ | Peptide 5 |
| 6 | IGKPYNSSGL | Peptide 6 |
| 7 | HNLGDQIGKPYNSSGL | Peptide 7 |
| 8 | GDQIGKPYNSSGL | Peptide 8 |
| 9 | GNMEQPHMDSRIGWLHNLGDQSSGLIGKPYN | E-pore peptide |
| 10 | NEQDRSGYHPMKWMSIILGGSGLNGPQNDLH | Scrambled control peptide |

It was tested whether synthetic molecular entities mimicking the 3D structure of these epitopes would compete and neutralize circulating anti-Ro Abs preventing QTc prolongation in an animal model of anti-Ro Abs induced QTc prolongation. Anti-Ro Ab-targeted epitopes in hERG-K channels resemble either linear or conformational pathogenic epitopes on Ro52 antigen, which are targeted by anti-Ro Abs. The mimicry of these epitopes and the resultant cross-reactivity of anti-Ro Abs with hERG-K channel is responsible for anti-Ro Abs induced QTc prolongation and associated ventricular arrhythmias and sudden cardiac death.

The premise is that strategies to safely prevent QTc prolongation associated with anti-Ro Ab/hERG-K channel interactions may be clinically promising. Described herein are decoy peptides designed bearing epitopes mimicking cross-reactivity with hERG-K channel and Ro52 epitopes that may be capable of neutralizing circulating anti-Ro Abs in the guinea-pig animal model of anti-Ro Ab associated QTc prolongation (Yue Y, et al., Circulation. 2015; 132:230-40). The results are expected to demonstrate reversal and normalization of QTc prolongation in vivo using these decoy peptides.

Figure 2:
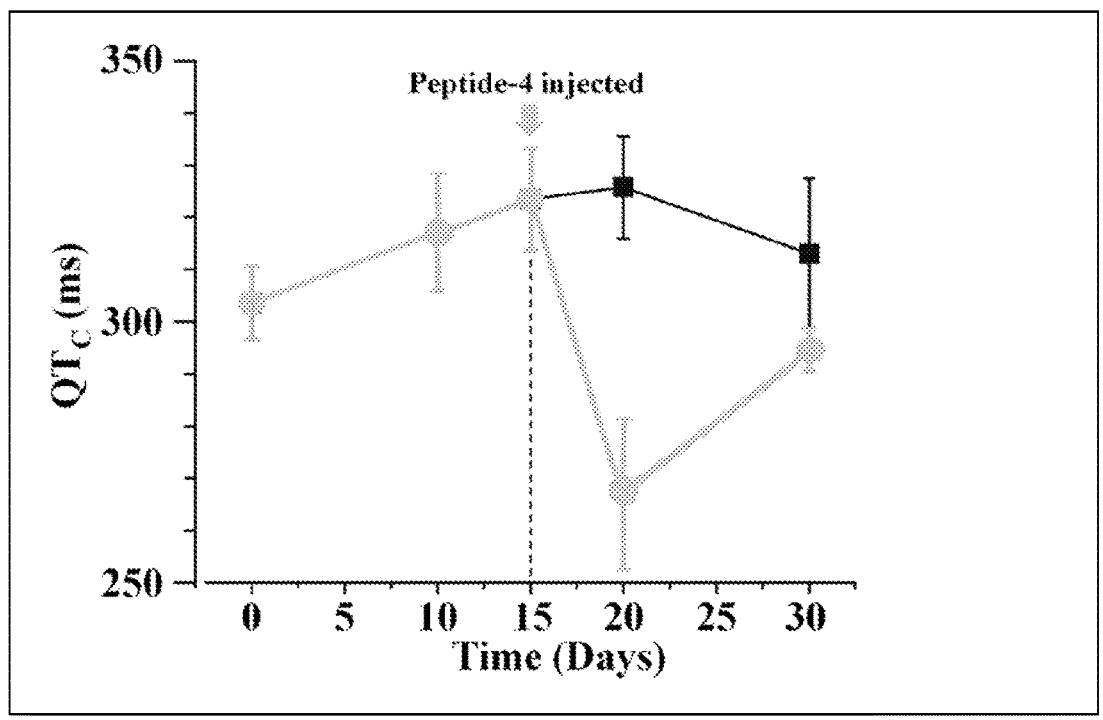
FIG. 2 shows the rescue and reversal of QTc prolongation in Ro-52 immunized guinea pigs. Animals were first injected with the antigen Ro52 to generate anti-Ro antibodies (grey circles). At baseline (black squares), QTc values increased over time for control guinea pigs. A one-time injection of a linear peptide-4 at day 15 resulted in drastic shortening of QTc, followed by recovery towards baseline by day 30.
Figure 6:
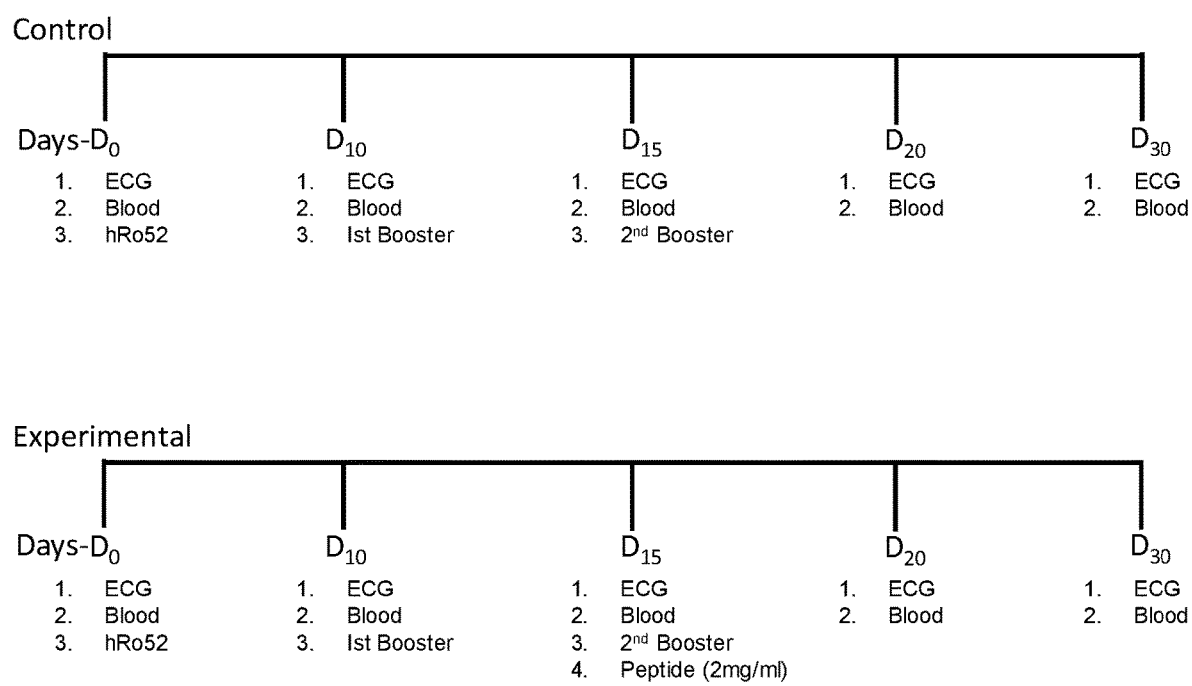
FIG. 6 shows the immunization and peptide administration protocol.

Immunization and peptide administration protocol. The overall experimental protocol for immunization and administration of the peptide used to generate data in FIG. 2 is shown in FIG. 6. Specifically, two group of guinea pigs (control and experimental) were first immunized subcutaneously initially on day 0 (Do) with Ro52 antigen followed by a booster at days 10 and 15, and anti-Ro antibodies levels were monitored by ELISA. The control group was not administered any peptide treatment except the immunization. The experimental group was injected with the linear peptide #4 (2 mg/kg) at day 15. ECGs including QTc were recorded at baseline (Do) and thereafter through day 30 (D30) as indicated in FIG. 6.

The data show that peptide-4 rescued and normalized the QTc interval of guinea-pigs immunized with Ro52 to generate anti-Ro Abs mimicking the clinical setting (FIG. 2, circles). However, control guinea-pigs which did not receive peptide-4 (squares) exhibited more abnormal QTc prolongation over time.

The experimental design is intended to demonstrate that designed decoy peptides are able to neutralize anti-Ro Abs in an in-vivo animal model and reverse QTc prolongation.

Design and Production of a Pharmaceutical Grade Synthetic Peptide.

The 3D structures of the decoy peptides capable of blocking the Ro52-elicited QTc prolongation in an animal model have been modeled by ab initio molecular modeling. Single-point mutants of each amino acid in the peptides that were active in vivo will be commercially synthesized and tested by ELISA for their binding to serum Abs from the Ro52 guinea pig model to map the epitope.

Testing of reversal of QTc prolongation in an in-vivo animal model of Autoimmune Associated QTc prolongation using rationally designed biologics. An established animal model for anti-Ro Abs associated QTc prolongation will be used, where guinea-pigs will be first immunized with Ro52 antigen. Eight groups (Table 2) will be used. Group 1 will be the positive control group of 6 guinea-pigs immunized with Ro52 antigen to allow the development of anti-Ro Abs and QTc prolongation. Group 2 of 12 guinea-pigs (2 subgroups of n=6 each) will be intravenously administered the decoy peptide at different concentrations (e.g., 2 mg/kg, n=6; 5 mg/kg, total n=18) at day 15, where anti-Ro Abs become detectable and continue with another daily similar dose of the decoy peptide until QTc is abrogated. This approach will be the equivalent of clinical preventive pharmacotherapy where the decoy peptide will neutralize the freely circulating anti-Ro Abs prior to their complete binding to the hERG-K channel. Group 3 of 12 guinea-pigs will be Ro52 immunized, and will be allowed to develop maximum QTc prolongation at day 60 and then the decoy peptide will be administered intravenously at a dose determined above to see if it is able to displace the Abs already bound to the hERG-K channel and thus reverse QTc prolongation. This scenario will be equivalent to clinical pharmacotherapy administered after the pathology has already taken place. Group 4 and group 5 will be administered the scrambled peptide as a control at day 15 and day 30 respectively. Group 6 is the sham control group injected with vehicle solution. Finally, for groups 7 and 8, the guinea-pigs will not be immunized with Ro52 antigen but rather the decoy peptides or the scrambled peptide will be administered alone to test whether they have any effect per se on QT interval in the absence of anti-Ro Abs.

TABLE 2

Experimental groups.

| Group 1 | Group 2 | Group 3 | Group 4 | Group 5 | Group 6 | Group 7 | Group 8 |
|---|---|---|---|---|---|---|---|
| Ro52 immunized | Ro52 immunized | Ro52 immunized | Ro52 immunized | Ro52 immunized | Sham | Peptides alone | Scrambled Peptides alone |
| Positive control n = 6 | Experimental peptides Ro52 immunized Experimental + Biologic peptide administered daily starting at day 15 to day 30. n = 6 for 2 mg/kg; n = 6 for 5 mg/kg; animals per peptide = 12 Total animals for 8 experimental peptides = 12 × 8 = 96 | Experimental peptides Ro52 immunized Experimental + Biologic peptide administered at day 30. n = 6 for 2 mg/kg; n = 6 for 5 mg/kg; animals per peptide = 12 Total animals for 8 experimental peptides = 12 × 8 = 96 | Scrambled Peptide Ro52 immunized + Scrambled peptide administered daily starting at day 15 to day 30. n = 6 for 2 mg/kg; n = 6 for 5 mg/kg; Animals per peptide = 12 | Scrambled Peptide Ro52 immunized + Scrambled peptide administered at day 30. n = 6 for 2 mg/kg; n = 6 for 5 mg/kg; Animals per peptide = 12 | Control Sham injected with vehicle solution (n = 6) | Control 8 peptides at the effective dose injected with vehicle solution each (n = 6 × 8 = 48) | Control Scrambled peptide injected at highest dose with vehicle solution (n = 6) |

Example 2: Experimental Design of the Complex Monobody/Peptide 4

Described herein is the design of the monobody/peptide 4 and its administration to Ro52 immunized guinea-pigs.

The experimental design includes 1) structural evaluation/molecular modeling of the candidate peptide, 2) a computational screen for protein domains that are suitable to fuse to the peptide, 3) computer-aided protein engineering of the peptide into said domain(s), 4) production of the DNA/gene for the thusly designed protein biologic, 5) expression of the DNA/gene for the thusly designed biologic in *E. coli* bacteria, and 6) purification of milligram amounts of the biologic candidate for guinea pig electrophysiological studies.

Figures 3A, 3B, 3C:
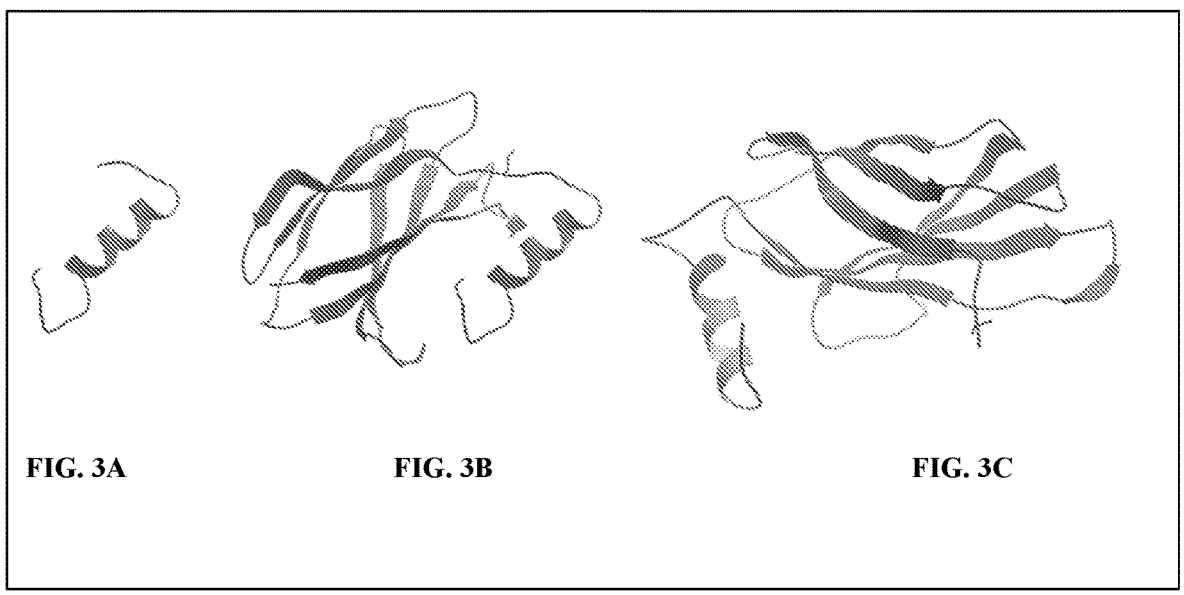
FIGS. 3A-C show the structure of peptide 4.

Results. Modeling: ab initio structure prediction was used to determine the dynamic structure of peptide 4. A full conformational search was performed and each conformation was evaluated for van der Waals, electrostatics, entropy and solvation energy. The lowest energy conformation is the likely biological structure and is shown in FIG. 3.

A computational screen (computer program) was performed through every domain in the Protein Data Bank, using the criteria: a) small, stable autonomous domain, b) expressed in *E. coli* in the crystal structure, c) N-terminal peptide structure from modeling is compatible with an insertion point in the domain, d) from a protein currently FDA-approved or in clinical trials. The top ranked protein domain in this screen was the fibronectin type III repeat 10 domain (monobody), which has been engineered as a single domain "mini antibody".

Ab initio structure prediction was used to determine the dynamic structure of peptide 4 as a fusion protein with the monobody (computer-aided protein engineering). The results show that peptide 4 can be attached at both the N and C termini of the monobody without destabilizing it. The N-terminal attachment has the advantage of disrupting the functional sites of the monobody that is engineered to bind targets, but has the disadvantage of being a riskier construct for protein expression.

The DNA/gene for both the N- and C-terminal designs were synthesized.

*E. coli* was transformed to take up the DNA/gene of the N-terminal design and grown and selected for stable expression of the protein.

The protein was purified in small scale using an ion exchange column and gel filtration. Soluble protein was obtained, but could not be verified by mass spectroscopy. The protein concentration in the purified fractions dropped in half within a few days, suggesting that, although it was minimally soluble, it was not sufficiently soluble for in vivo studies.

Example 3: Experimental Design for the Guinea-Pig Immunization with Anti-Ro52 and Treatment with Monobody/Peptide 4

Figure 4:
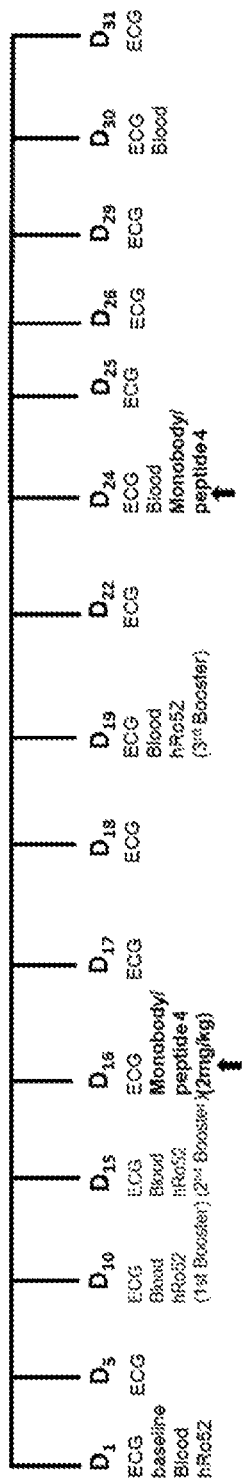
FIG. 4 shows the timeline for the experimental protocol for a) the electrocardiographic (ECG) recordings; b) the blood withdraw for antibody testing; 3) the administration of Ro52 antigen; 4) the boosters and 5) the administration of the monobody/peptide 4 indicated by the arrows.

A control group 1 of 8 guinea-pigs were immunized with Ro52 antigen according to the protocol shown in FIG. 4 to allow for the development of anti-Ro Abs which cause QTc prolongation on the electrocardiogram (ECG).

An experimental group 2 of 5 Ro52-immunized guinea-pigs were intraperitoneally administered the monobody/peptide 4 biologic at 2 mg/kg first at day 16, and anti-Ro Abs were detectable. A second injection of the monobody/peptide 4 biologic at 2 mg/kg was administered on day 24 (FIG. 4). The QTc is monitored over a period of 31 days. This approach is the equivalent of clinical preventive pharmacotherapy where the monobody/peptide 4 is presumed to neutralize the freely circulating anti-Ro Abs prior to their complete binding to the HERG-K channel.

Figure 5:
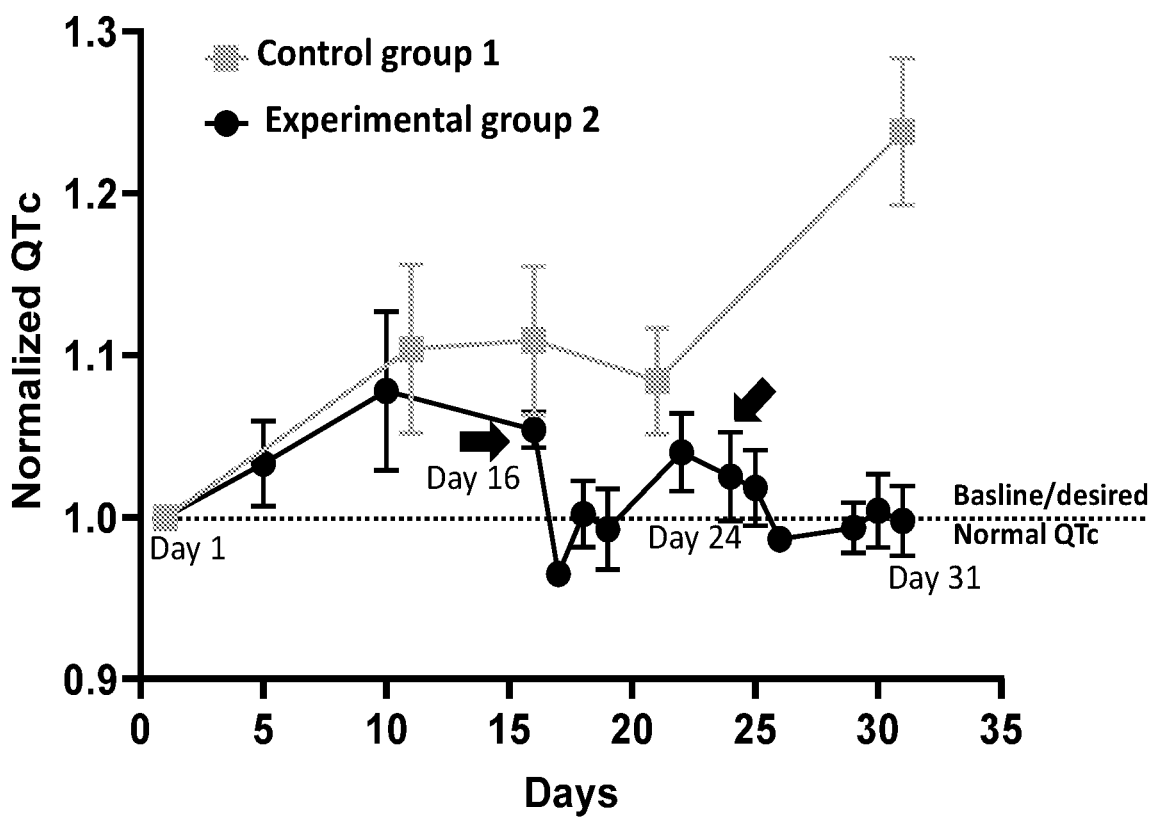
FIG. 5 shows the normalized QTc vs the experimental days. At day 1, baseline ECG was first recorded and the values of the normalized QTc are plotted over time. The control group 1 which was immunized by the Ro52 antigen only and not with the monobody/peptide 4, showed an increase in QTc over time (grey squares). The experimental group 2 (black circles) received the first injection of the monobody/peptide 4 on day 16 (black arrow) and the second injection on day 24 (black arrow). Since the administration of the monobody peptide 4, the QTc values remained around the normal values until the last day (day 31) of ECG recordings. The dashed line illustrates the baseline normal QTc.

Results. FIG. 5 shows the normalized QTc in the Y-axis and the intervention days in the X-axis. At day 1, baseline ECG was first recorded and the values of the normalized QTc are plotted over time. The control group 1, which was immunized by the Ro52 antigen and not with the monobody/peptide 4, showed an increase in QTc over time (grey graph in FIG. 5). This increase was from QTc=291.7±1.2 msec at basal condition in day 1 to QTc=360.8±13.6 msec at day 31

(ΔQTc=69 msec) and is due to the increasing levels of anti-Ro52 Abs which block the HERG-K channel and cause QTc prolongation.

Experimental group 2 received both the Ro52 antigen and the monobody/peptide 4 as indicated in FIGS. 4 and 5. There was a progressive increase in QTc until Day 16 when the monobody/peptide 4 was administered where the QTc dropped sharply and stayed around the baseline normal QTc. The QTc values started increasing slightly until the second injection of the monobody/peptide 4 at Day 24 where the QTc again remained within the normal baseline values until the $31^{st}$ day (from QTc=290±6.2 during baseline to QTc=289.6±3.8 at day 31 with a (ΔQTc=−1 msec).

Collectively, these results clearly demonstrate that the treatment of Ro52-immunized guinea-pigs with the monobody/peptide 4, normalized the QTc values and prevented the otherwise continuous increase in QTc seen in group 1 (control) which was not treated with monobody/peptide 4. The combined monobody/peptide 4 mimicking the 3D configuration of the peptide 4 appears more long-lasting than the linear peptide 4; in this case 15 days with only 2 injections of the monobody/peptide 4. These data are first to demonstrate the potential therapeutic value of the monobody/peptide 4 in the treatment of autoimmune associated long QT syndrome.

What is claimed is:

1. A peptide consisting of the sequence of GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), or GDQIGKPYNSSGL (SEQ ID NO: 8), wherein the peptide has at least one amino acid that has an acetyl group, a fluorenylmethyoxy carbonyl group, a formyl group, a palmitoyl group, a myristyl group, a stearyl group, or a polyethylene glycol, and wherein the peptide inhibits the binding of anti-Ro antibodies to a hERG potassium channel extracellular pore region.

2. The peptide of claim 1, wherein the peptide consists of the sequence GNMEQPHMDSRIGWLHNLGDQ (SEQ ID NO: 4).

3. A composition comprising a fibronectin type III (Fn3) monobody and a peptide, wherein the peptide consists of the sequence of GNMEQPHMDSRI (SEQ ID NO: 1), GWLHNLG (SEQ ID NO: 2), DQIGKPYNSSGL (SEQ ID NO: 3), GNMEQPHMDSRIGWLHNLGDQ (SEQ ID NO: 4), HMDSRIGWLHNLGDQ (SEQ ID NO: 5), IGKPYNSSGL (SEQ ID NO: 6), HNLGDQIGKPYNSSGL (SEQ ID NO: 7), or GDQIGKPYNSSGL (SEQ ID NO: 8), wherein the Fn3 monobody is conjugated to the peptide and does not destabilize the peptide, and wherein the peptide inhibits the binding of anti-Ro antibodies to a hERG potassium channel extracellular pore region.

4. The composition of claim 3, wherein the peptide is conjugated to the C-terminus of the Fn3 monobody.

5. The composition of claim 3, wherein the peptide consists of the sequence GNMEQPHMDSRIGWLHNLGDQ (SEQ ID NO: 4).

* * * * *

```
SEQUENCE LISTING

<160> NUMBER OF SEQ ID NOS: 11

<210> SEQ ID NO 1
<211> LENGTH: 12
<212> TYPE: PRT
<213> ORGANISM: Artificial Sequence
<220> FEATURE:
<223> OTHER INFORMATION: Synthetic construct

<400> SEQUENCE: 1

Gly Asn Met Glu Gln Pro His Met Asp Ser Arg Ile
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic construct

<400> SEQUENCE: 2

Gly Trp Leu His Asn Leu Gly
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic construct

<400> SEQUENCE: 3

Asp Gln Ile Gly Lys Pro Tyr Asn Ser Ser Gly Leu
1               5                   10

<210> SEQ ID NO 4
<211> LENGTH: 21
<212> TYPE: PRT
<213> ORGANISM: Artificial Sequence
<220> FEATURE:
<223> OTHER INFORMATION: Synthetic construct

<400> SEQUENCE: 4

Gly Asn Met Glu Gln Pro His Met Asp Ser Arg Ile Gly Trp Leu His
1               5                   10                  15

Asn Leu Gly Asp Gln
            20

<210> SEQ ID NO 5
<211> LENGTH: 15
<212> TYPE: PRT
<213> ORGANISM: Artificial Sequence
```

```
<220> FEATURE:
<223> OTHER INFORMATION: Synthetic construct

<400> SEQUENCE: 5

His Met Asp Ser Arg Ile Gly Trp Leu His Asn Leu Gly Asp Gln
1               5                   10                  15

<210> SEQ ID NO 6
<211> LENGTH: 10
<212> TYPE: PRT
<213> ORGANISM: Artificial Sequence
<220> FEATURE:
<223> OTHER INFORMATION: Synthetic construct

<400> SEQUENCE: 6

Ile Gly Lys Pro Tyr Asn Ser Ser Gly Leu
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Synthetic construct

<400> SEQUENCE: 7

His Asn Leu Gly Asp Gln Ile Gly Lys Pro Tyr Asn Ser Ser Gly Leu
1               5                   10                  15

<210> SEQ ID NO 8
<211> LENGTH: 13
<212> TYPE: PRT
<213> ORGANISM: Artificial Sequence
<220> FEATURE:
<223> OTHER INFORMATION: Synthetic construct

<400> SEQUENCE: 8

Gly Asp Gln Ile Gly Lys Pro Tyr Asn Ser Ser Gly Leu
1               5                   10

<210> SEQ ID NO 9
<211> LENGTH: 31
<212> TYPE: PRT
<213> ORGANISM: Artificial Sequence
<220> FEATURE:
<223> OTHER INFORMATION: Synthetic construct

<400> SEQUENCE: 9

Gly Asn Met Glu Gln Pro His Met Asp Ser Arg Ile Gly Trp Leu His
1               5                   10                  15

Asn Leu Gly Asp Gln Ile Gly Lys Pro Tyr Asn Ser Ser Gly Leu
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Synthetic construct

<400> SEQUENCE: 10

Asn Glu Gln Asp Arg Ser Gly Tyr His Pro Met Lys Trp Met Ser Ile
1               5                   10                  15

Ile Leu Gly Gly Ser Gly Leu Asn Gly Pro Gln Asn Asp Leu His
            20                  25                  30
```

```
<210> SEQ ID NO 11
<211> LENGTH: 94
<212> TYPE: PRT
<213> ORGANISM: Artificial Sequence
<220> FEATURE:
<223> OTHER INFORMATION: Synthetic construct

<400> SEQUENCE: 11

Val Ser Asp Val Pro Thr Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90
```